(12) United States Patent
Shalon

(10) Patent No.: US 8,230,865 B2
(45) Date of Patent: Jul. 31, 2012

(54) PALATAL IMPLANT

(75) Inventor: Tidhar Shalon, Tel-Aviv (IL)

(73) Assignee: SVIP 1 LLC, Palo Alto, CA (US)

( * ) Notice: Subject to any disclaimer, the term of this patent is extended or adjusted under 35 U.S.C. 154(b) by 413 days.

(21) Appl. No.: 12/602,100

(22) PCT Filed: May 26, 2008

(86) PCT No.: PCT/IL2008/000713
§ 371 (c)(1),
(2), (4) Date: Nov. 26, 2009

(87) PCT Pub. No.: WO2008/146278
PCT Pub. Date: Dec. 4, 2008

(65) Prior Publication Data
US 2010/0174370 A1    Jul. 8, 2010

Related U.S. Application Data

(60) Provisional application No. 60/924,811, filed on May 31, 2007.

(51) Int. Cl.
*A61C 5/14* (2006.01)
(52) U.S. Cl. .................................... 128/859; 128/921
(58) Field of Classification Search .................. 128/848, 128/859, 921, 897–898; 600/24
See application file for complete search history.

(56) References Cited

U.S. PATENT DOCUMENTS

| 4,969,906 | A | | 11/1990 | Kronman |
| 5,924,422 | A | * | 7/1999 | Gustafson ..................... 128/846 |
| 5,979,449 | A | | 11/1999 | Steer |
| 2004/0045555 | A1 | | 3/2004 | Nelson et al. |
| 2006/0195169 | A1 | | 8/2006 | Gross et al. |
| 2006/0207607 | A1 | | 9/2006 | Hirotsuka et al. |

FOREIGN PATENT DOCUMENTS
WO   WO 2008/146278   12/2008

OTHER PUBLICATIONS

SR and WO of Jan. 12, 2009.
International Search Report Dated Jan. 12, 2009 From the International Searching Authority Re.: Application No. PCT/IL2008/000713.
Written Opinion Dated Jan. 12, 2009 From the International Searching Authority Re.: Application No. PCT/IL2008/000713.
International Preliminary Report on Patentability Dated Jan. 28, 2010 From the International Bureau of WIPO Re.: Application No. PCT/IL2008/000713.

* cited by examiner

*Primary Examiner* — Patricia Bianco
*Assistant Examiner* — Camtu Nguyen

(57) ABSTRACT

A device for modifying an eating behavior of a subject is provided. The device is configured for implantation within the oral cavity and is capable of altering a palatal vault of the subject.

9 Claims, 2 Drawing Sheets

PALATAL IMPLANT

RELATED APPLICATIONS

This application is a National Phase Application of PCT Application No. PCT/IL2008/000713 having International Filing Date of May 26, 2008, which claims priority from U.S. Provisional Patent Application No. 60/924,811, filed on May 31, 2007. The contents of the above Applications are all incorporated herein by reference.

FIELD AND BACKGROUND OF THE INVENTION

The present invention relates to devices and methods for modifying an eating behavior of a subject, more particularly, to an implant which alters the shape/size of the palatal vault in a manner which modifies the eating behavior of the subject.

Torus palatinus (pl. palatal tori) is a small bony growth on the hard palate which is more common in early adult life and can increase in size over time (FIG. 1). Although some research suggest palatal tori to be an autosomal dominant trait, it is generally believed that palatal tori are caused by several factors.

Tori are categorized by their appearance. Flat tori are located on the midline of the palate and extend symmetrically to either side. Spindle tori have a ridge located at their midline. Nodular tori have multiple bony growths that each have their own base. Lobular tori have multiple bony growths with a common base.

Palatal tori usually do not require treatment, although it is possible for ulcers to form on the area of the tori due to repeated trauma. If removal of the tori is needed (e.g. for denture fitting), surgery can be done to reduce the amount of bone present.

Palatal tori are common among thin people. The reduction of palatal vault volume caused by these bony protrusions reduces food gulping and slows food intake while increasing food savoring, thereby allowing satiety signals to trigger on smaller amounts of food.

Devices which attempt to mimic the effect of palatal tori have been previously described. U.S. Pat. No. 5,924,422 and published U.S. App. 20050287495 both describe intra-oral devices which are fitted against the hard palate to effectively decrease oral cavity volume. The device described in U.S. App. 20050287495 has shown efficacy in reducing food consumption in clinical trials.

Although such a device can slow food intake, it is designed as a removable intra-oral device and as such it is limited by issues associated with compliance, comfort, sensation of the tongue against plastic as opposed to live tissue, adverse orthodontic effects typically effecting intra-oral devices.

While reducing the present invention, the present inventors have postulated that an eating behavior of a subject can also be modified by altering the shape and/or size of the palatal vault with an implantable device. Such a configuration is advantageous in that it traverses the limitations inherent to prior art intra-oral devices while providing a long lasting, and optionally reversible solution to the problem of eating disorders.

SUMMARY OF THE INVENTION

According to one aspect of the present invention there is provided a device for modifying an eating behavior of a subject, the device being configured for implantation within the oral cavity and altering a volume thereof.

According to another aspect of the present invention there is provided a method of modifying an eating behavior of a subject comprising implanting a device within the oral cavity, the device being capable of reducing a volume of the oral cavity of the subject.

According to further features in preferred embodiments of the invention described below, implantation of the device alters a shape and/or size of the palatal vault.

According to still further features in the described preferred embodiments implantation of the device lowers at least one region of the roof of the oral cavity of the subject.

According to still further features in the described preferred embodiments at least one region is the palatal midline.

According to still further features in the described preferred embodiments the device is configured for implantation against the hard palate.

According to still further features in the described preferred embodiments the device is configured for implantation within the maxillary gums.

According to still further features in the described preferred embodiments the device is configured as an inflatable bladder.

According to still further features in the described preferred embodiments the device is configured as a solid implant.

According to still further features in the described preferred embodiments the device is configured as a bulking composition.

According to still further features in the described preferred embodiments the device is configured as a silicone implant.

According to still further features in the described preferred embodiments the device is implanted under the gingiva at the hard palate.

According to still further features in the described preferred embodiments the device is anchored to the hard palate.

According to still further features in the described preferred embodiments implanting is effected by a soft tissue incision.

The present invention successfully addresses the shortcomings of the presently known configurations by providing an implantable, eating behavior-modifying device.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
FIG. 1 is an image of a torus palatinus in a subject.

The present invention is of an implant positionable within the oral cavity and configured for altering a shape or size of the palatal vault or a rigidity of a wall defining the palatal vault.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Anatomical modifications induced by palatal tori have been associated with modified eating behavior. Intra oral devices designed for mimicking the effects of palatal tori on the palatal vault have been shown to be effective in reducing food consumption in tested individuals (Scientific Intake Inc.). Although such devices can reduce food consumption, their intra oral positioning might lead to discomfort, adverse orthodontic effects as well as low compliance.

The present inventors propose that modifications to palatal vault anatomy can also be effected using implantable devices which are free of limitations associated with oral or dental appliances.

Thus, according to one aspect of the present invention here is provided a device for modifying an eating behavior of a subject (e.g. a mammal such as a human).

The device is selected suitable for implantation within the oral cavity and as such is composed of, or coated with a biocompatible material; the device is configured capable of altering a palatal vault of the subject.

As used herein the phrase "altering a palatal vault" refers to altering a shape or volume defined by the palatal vault, or altering the rigidity of the walls defining the palatal vault (e.g. decreasing the rigidity of the roof of the palatal vault via a soft implantable body). By altering a palatal vault, the volume of the oral cavity is likewise altered. In such altering, the tongue of the user still rests against the normal mucosal tissue (gingiva) covering the hard palate, leading to a natural feeling in the mouth.

Numerous configurations of the present device are contemplated herein, such configurations are dependent on the site of implantation (e.g. hard palate, maxillary gums etc) and the anatomy of the individual as well as the effect desired.

In general, when the device is implanted in the hard palate (preferably under the submucosa and/or the palatal glands and adjacent to the bone), the device body is configured such that it lowers at least a region of the hard palate (e.g. the palate midline) by about 0.2-2 cm. Such a device can be configured as a hemispherical or ovoid body and be fabricated from bone/cartilage/fat grafts, ivory, acrylic, metals/alloys, polymeric materials such as polytetrafluoroethylene (PTFE), silicone, nylon mesh, expanded PTFE, high-density polyethylene, hydroxyapatite compounds and the like [see, Adams Otolaryngol Clin North Am. 1987 Nov. 20 (4):913-30]. The device can also be configured as a solid or hollow implant. Solid implants of various hardness are contemplated herein. For example, a solid silicone implant can have a Shore A value of 0-100. Solid implant also encompass covered or exposed, open or closed-cell foam-like configurations fabricated from, for example, ePTFE, polyurethane or silicone. Coverings of such implants can be microporous to allow water to enter into their core to cause them to swell while not allowing cells or other biological material to enter. Other forms of solid implants include deployable structures which can be expanded at the site of implantation (e.g. similar to stent expansion) and can include a mechanism for adjusting size or volume. Typical examples include a self-expanding metallic stent covered by a flexible silicone membrane. A hollow implant can take the form of a gas (e.g. air or CO2), fluid (e.g. saline) or gel (e.g. silicone gel) filled silicone bladder which can include a fill/drain valve/septum for adjustability post implantation via a superficial injection. Examples of such implants include the FulFil™ implant made by Evera Medical (formerly Juva Medical). Gas filled implants can be inflated using an external or internal self contained gas source (see, for example, US 20060069403).

In an alternative embodiment, the bladder of the implantable device can be temporarily or permanently inflated in real time by a fluid pump in fluid communication with the bladder. The fluid pump can be driven via a motorized mechanism or by the action of the user, for example chewing motion inflates the bladder, which is then slowly deflated over time. This achieves the goals of reducing the palate during eating, but not at other times of the day or night, thereby minimizing any unnatural feelings associate with a reduced oral cavity volume. Such mechanisms are well known in the art (see for example the NeoSphincter for fecal incontinence by AMS, American Medical Systems).

In any case, the size and location of the implanted device are selected such that the palatal vault is altered in one or more of the parameters described above.

For example, reduction of the volume defined by the palatal vault by 0.5 to 7 cm$^3$, can be effected by implanting a suitable configuration of the present device under the soft tissue lining of the hard palate and adjacent to the hard palate bone, effectively lowering the palatal vault roof by 0.2-2 cm. An implant for such purposes can be shaped as a spherical or elliptical convexity and is preferably configured as a fillable and adjustable bladder (see FIG. 2 below for additional detail).

Many techniques are known in the art for delivering the implant, whether in final form or deflated or desiccated to the implant site. The implant can be introduced into the tissue through a tissue penetration approach, e.g. a small incision, needle puncture and/or blunt dissection (with saline injection with a needle, by needle-less injection of saline through a fluid jet nozzle, or by blunt edged tissue separator) for creating a pocket for insertion of the device. The implant can be injected into the implant position using a hollow delivery needle and a plunger (see for example the technology used by Restore Medical for soft palate stiffening). Alternatively the implant can be attached to the back of a needle and pulled through the tissue in one direction and the needle removed through a separate exit hole leaving the implant in the tissue in the path of the needle (the FulFil™ implant of Evera Medical is an example of such a delivery approach).

Compositions, such as particle slurries, biomolecule solutions and in-situ forming polymers/gels [vinylpolysiloxane (VPS) or alginate] can be injected into the site of implantation using a 16-20 gauge needle or needle-free via a fluid jet nozzle directly or into a biocompatible membrane, say of silicone or ePTFE, that isolates the injectable material from contact with the tissue.

Other materials which can be used with the preparation of the present invention include, but are not limited to, acrylate polymers (e.g. polyacrylamide), sodium hyaluronate; polyvinyl alcohol (PVA); hydroxypropylmethyl cellulose (HPMC) and its derivatives including hydroxyalkyl cellulose, sodium carboxymethyl cellulose, hydroxyethyl cellulose, hydroxypropyl cellulose, methylhydroxypropyl cellulose, methyl cellulose and ethylhydroxyethyl cellulose; thermoset elastomers, agar, polyurethane foam, expanded polytetrafluoroethylene (ePTFE), polyethylene implants, hydroxyapatite implants, injectable hydroxyapetite paste, hydrophilic polyacrylamide gel, and the like. Additional in-situ forming polymers that are contemplated for use with this invention are well known in the art (see for example Kissel, et. Al. European Journal of Pharmaceutics and Biopharmaceutics 58 (2004) 445-455).

Additives that can be incorporated into the preparation include, but are not limited to, viscosity modifiers, gellation retarding agents, colorants, indicators, tackifiers, plasticizers, antioxidants, hydrocolloids (typically in the form of particles), radio-opaque markers and the like. For example, MagicFoamCord™ made by Coltene Whaledent is a VPS formulation that traps bubbles inside during setting and creates a porous silicone foam material that is suited to increase volume and extrusion-resistance of the implant.

Additional implant materials contemplated for use in this invention include biopolymers such as ethinyl-vinyl-alcohol in an organic liquid carrier such as DMSO with radio-opaque contrast agent such as tantalum. Ethinyl-vinyl-alcohol, for example, precipitates into spongy mass in tissue and is non-biodegradable, not antigenic, and has no migration through vessels. Such a material can provide the required rigidity when injected into the tissue using an injection needle.

Use of swellable desiccated hydrogels is also contemplated herein. Thus, the device can include a desiccated hydrogel such as desiccated polyacrylamide, desiccated alginate, laminaria and the like. In this embodiment, the desiccated implant can be introduced through a delivery needle or sharpened and pushed into the tissue of interest and the tissue can close around the back end of the implant thereby sealing it completely in the tissue. The implant will then expand due to uptake of interstitial fluid via osmotic pressure differentials thereby stabilizing itself in the tissue and preventing extrusion. An example of a suitable implant material is a radio-opaque, removable hydrogel such as polyacrylonitril which can be inserted as a thin and long implant (shaped and sized like a toothpick) and which expands to 90% of its final shape and volume (shaped like a gel capsule) within 6 hours of residing in the tissue. The change in volume and shape is fully controllable by proper design of the implant. The change in shape can serve to embed the implant in the tissue to prevent extrusion. Explantation of the device, if desired, can be via a small soft tissue incision and retraction of the implant along the entry path.

It is envisioned that one or more implants can be utilized to reduce the oral cavity volume. For example a series of elongated implants can be inserted in parallel in the hard palate region separated by several millimeters or centimeters. Alternatively, individual implants, each only a few cubic millimeters or centimeters in volume can be implanted throughout the hard palate region and together constitute sufficient oral cavity reduction. An advantage to this is the relative ease of inserting and removing small implants.

The implant can be designed to allow for easy removal through a small incision, similar to the size required for insertion. For this purpose, the insert may be deflated if it was previously inflated.

Figure 2:
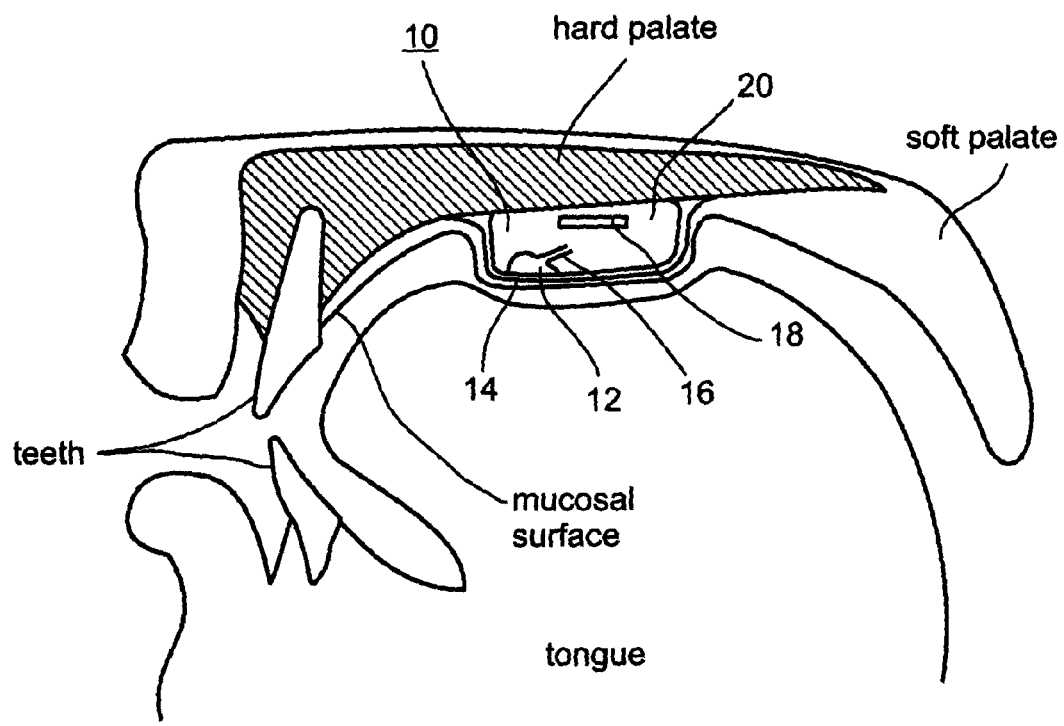
FIG. 2 illustrates a medial sagittal view of one embodiment of an implant designed and configured according to the teachings of the present invention positioned in the region of the hard palate.

Referring now to the drawings, FIG. 2 illustrates one embodiment of the present device which is referred to herein as device 10. Device 10 is shown implanted in the hard palate under the soft tissue layer.

Device 10 shown in FIG. 2 is configured as an adjustable bladder which is suitable for implantation in the hard palate and functions in lowering the roof of the hard palate thereby reducing the volume thereof.

Device 10 is preferably adjustable following implantation and as such is configured as an expandable stent-like device or fluid/gel filled bladder. The adjustability feature of the present device could be important in palatal implantation, since oral cavity anatomy varies from one individual. It is important that the device achieve its intended function while being tolerable by the subject. Thus, it might be necessary to adjust device dimensions following implantation to achieve a balance between operability and tolerability.

In the case of a fluid/gel filled bladder, device 10 further includes a valve assembly 12 which includes a septum 14 and a fluid conduit 16 communicating between septum 14 and device body 20. Device 10 can also contain a hard needle stop 18 to prevent the filling needle from puncturing the distal surface of device body 20.

Valve assembly 12 can be implanted along with device body 20 or elsewhere (e.g.

in the soft palate). Septum 14 is preferably implanted under the soft tissue and is designed to be accessible by a needle. Metal or magnetic elements around the septum or tattooing of the skin surface next to the site of implantation can aid the physician in finding and accessing septum 14. Such techniques are known in the art, for example inflatable laparoscopically-implanted gastric bands ("LAP Bands").

In an alternative embodiment, device body 20 includes a sealable shell which seals following puncturing, this enables filling/draining of device body 20 without use of a dedicated valve assembly.

An example of a technology that can be adapted for constructing valve assembly 12 is the Becker valve used in adjustable breast expander/implant (Mentor corp.—www.mentorcorp.com). A further example of a technology that can be adapted for constructing a suitable implant is the small tissue expanders made by McGhan Medical (Santa Barbara, Calif.).

Device 10 can also include bone or tissue anchoring elements to prevent migration of device body 20 in the tissue. Examples of such anchors include hooks or miniature bone screws. Anchoring can also be achieved via fibrosis-inducing coatings or by ridges or a rough surface finish on the outer surface of device body 20 (similar to the surface textures/patterns used in breast implants). Since the hard palate participates in the breakdown of food, the present inventors believe that a device 10 which is configured having a soft device body (solid or foam material of Shore A of 5-50 or a fluid filled bladder) can further impact an eating behavior of the subject. Implantation of such a device against the hard palate bone will reduce the hardness or rigidity of the palatal vault roof and as such reduce the ability of the oral cavity to break down food during chewing which will lead to increased chewing, longer eating times, earlier satiety and thus less food intake.

As used herein the term "about" refers to ±10%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for modifying an eating behavior of a subject, the device being configured for implantation under oral cavity tissue and altering volume of said oral cavity, wherein said device is configured as an inflatable bladder.

2. The device of claim 1, wherein implantation of the device alters a shape and/or size of the palatal vault or hardness of the palate.

3. The device of claim 1, wherein implantation of the device lowers at least one region of the hard palate of said oral cavity of the subject.

4. The device of claim 3, wherein said at least one region is the palatal midline.

5. The device of claim 1, being configured for implantation against the hard palate bone.

6. The device of claim 1, being configured for implantation within the maxillary gums.

7. A method of modifying an eating behavior of a subject comprising implanting a device under oral cavity tissue and anchoring said device to the hard palate bone, said device being capable of reducing a volume of said oral cavity of the subject.

8. The method of claim 7, wherein said device is implanted under the soft tissue of the hard palate.

9. The method of claim 7, wherein said implanting is effected by a soft tissue penetration.

* * * * *